United States Patent [19]
Abbott

[11] 4,290,892
[45] Sep. 22, 1981

[54] ANION EXCHANGE CHROMATOGRAPHIC SEPARATION OF POLYFUNCTIONAL COMPOUNDS

[75] Inventor: Seth R. Abbott, Concord, Calif.
[73] Assignee: Varian Associates, Inc., Palo Alto, Calif.
[21] Appl. No.: 16,847
[22] Filed: Mar. 2, 1979

Related U.S. Application Data

[63] Continuation-in-part of Ser. No. 953,380, Oct. 23, 1978.
[51] Int. Cl.$^3$ ............................................. B01D 15/08
[52] U.S. Cl. ................................... 210/656; 210/198.2
[58] Field of Search ................. 210/31 C, 198C, 635, 210/656, 659, 198.2

[56] References Cited
U.S. PATENT DOCUMENTS

| | | | |
|---|---|---|---|
| 3,664,967 | 5/1972 | Stehl | 210/31 C |
| 3,808,125 | 4/1974 | Good | 210/31 C |
| 3,984,349 | 10/1976 | Meiller | 210/31 C |
| 4,043,905 | 8/1977 | Novotny et al. | 210/31 C |
| 4,118,316 | 10/1978 | Talley et al. | 210/31 C |

OTHER PUBLICATIONS

Introduction to Modern Liquid Chromatography by Snyder et al., John Wiley & Sons, N.Y., N.Y., pp. 287–299 and 318–320 relied on, 1974.

Primary Examiner—John Adee
Attorney, Agent, or Firm—Stanley Z. Cole; Pauline A. Clarke

[57] ABSTRACT

A weak anion exchange composition useful in polyfunctional compound chromatographic separations comprises an inert porous particle having a tetra-substituted silane material fixedly attached by covalent bonding to the surface thereof. A process for synthesizing the weak anion exchange composition is disclosed together with methods for separation of polyfunctional compounds and their isomers using a column packed with such weak anion exchange composition.

14 Claims, No Drawings

ANION EXCHANGE CHROMATOGRAPHIC SEPARATION OF POLYFUNCTIONAL COMPOUNDS

CROSS-REFERENCE TO RELATED APPLICATIONS

This is a continuation-in-part of Application Ser. No. 953,380, filed Oct. 23, 1978.

BACKGROUND OF THE INVENTION

Compositions in which an alkyl or aryl substituent is affixed to the surface of siliceous materials by covalent chemical bonding with the resultant bonded materials being used for chromatography are known to the prior art. Exemplary of this type of prior art is Locke et al, *Analytical Chemistry*, Vol. 44, No. 1, pages 90–92 (1972). It is also known to react a siliceous surface with monohalogenated silanes, silazines or silylamines, or with monoalkoxy or monoacetoxysilanes, and then to cause a chemical modification of the reaction product. This type of prior art is illustrated by U.S. Pat. No. 4,043,905 to Novotny et al.

The use of tetra-substituted amino silane compositions covalently bonded to the surface of siliceous materials is also known. Majors, *Journal of Chromatographic Science*, Vol. 12, 767 (1974), used such a bonded phase in the "normal" mode for separation of azo compounds and polar steroids using organic solvents.

Partial resolution of biologically important mixtures of adenosine monophosphate isomers was achieved by Arendes et al., *Journal of Chromatography*, Vol. 140, 118 (1977).

Separation of the 2'- and 3'-isomers of adenosine monophosphate and guanosine monophosphate was achieved by Kratovich and Roe, *Journal of Chromatography*, Vol. 155, 407 (1978), using a strong anion exchange resin column.

Complete resolution of 2'-, 3'- and 5'-cytidine monophosphate was achieved in 15 hours by Ponnamperuma and Mack, *Science*, Vol. 148, 1221 (1965), using a Dowex-1 formate column. Further, Khym *Clinical Chemistry*, Vol. 21, 1245 (1975); *Journal of Chromatography*, Vol. 124, 415 (1976), used a gradient elution to achieve separation of ribo- from deoxyribonucleotides; however, complete elution of all nucleotides required 1–3 hours, and some pairs of ribo- and deoxyribonucleoside monophosphates were poorly resolved.

Brown et al., *Journal of Chromatography*, Vol. 112, 651 (1975); Vol. 152, 253 (1978), achieved separation of ribo- and deoxyribonucleoside mono-, di- and triphosphates using a silica-based, strong anion exchanger, but were not able to simultaneously obtain good resolution and a satisfactory analysis time.

Thus, although the prior art has achieved simultaneous resolution of some members of biologically important classes, it has not been able to rapidly and simultaneously separate bases, nucleosides and nucleotides, and isomers thereof, present in biological samples.

SUMMARY OF THE INVENTION

An object of the present invention is to provide a weak anion exchange composition comprising an inert porous particle to the surface of which a modified tetrasubstituted silane is attached by covalent chemical bonding.

Another object of the present invention is to provide a process for producing the weak anion exchange composition.

A further object of the present invention is to provide a novel method for separating polyfunctional compounds and isomers thereof by using this weak anion exchange composition packed in a column.

A further object of the present invention is to provide a novel method and apparatus for separation of polyfunctional compounds and isomers thereof using the weak anion exchange composition of this invention as a packing in a liquid chromatographic column.

A further object of the present invention is to provide a novel method and apparatus for separation of polyfunctional compounds and isomers thereof using the weak anion exchange composition of this invention as a column packing in a high pressure liquid chromatographic system such as that used in the liquid chromatographic system described by Achener, et al., in U.S. Pat. No. 3,985,021.

To accomplish the foregoing objects, this invention provides a weak anion exchange composition characterized by excellent, selective nucleic acid component separations, high phase loading and excellent stability in acidic phosphate buffers, comprising an inert microparticulate porous particle which in the chromatographic separations field generally has a maximum cross-sectional dimension in the range of from about 5 to about 20 microns with a modified tetra-substituted silane covalently bonded to the surface thereof.

This invention also provides a process for the manufacture of the weak anion exchange compositions. Where the inert porous particle is microparticulate silica, the manufacturing process for this weak anion exchange composition includes the steps of:

(a) reacting a tetra-substituted silane with an aqueous slurry of the silica, whereby a product is formed comprising the tetra-substituted silane covalently bonded to the silica;

(b) recovering, washing and drying the product;

(c) slurry packing a column with the product using a balanced density solvent system or any other appropriate packing solvent; and (d) washing the column with solvents, one of said solvents being phosphoric acid or equivalent.

Also, according to the present invention, a method is provided for separating polyfunctional compounds and isomers thereof. This method includes the steps of:

(a) placing a solution of the polyfunctional compound mixture on a column packed with the weak anion exchange composition; and (b) eluting the column with a gradient or isocratic mixture of aqueous buffer solutions or an aqueous buffer solution in an organic solvent.

DESCRIPTION OF THE INVENTION

The weak anion exchange composition of this invention comprises an inert porous particle to the surface of which is attached a modifed tetra-substituted silane by covalent chemical bonding. The particle has a size in the range of from about 5 to about 20 microns, with a size in the range from about 5 to about 10 microns being preferred.

The particle must be inert, i.e., it must be highly stable in organic solvents and in aqueous buffer solutions of pH about 2 to about 8 at ambient temperature. Exemplary organic solvents in which the particle must be highly stable are hexane, heptane, isooctane, cyclohexane, ethyl ether, dichloromethane, chloroform, methanol, isopropanol, ethanol, acetonitrile and tetrahydrofuran.

A particle that meets the above requirements may suitably be composed of microparticulate silica, alumina, a cross-linked dextran or a cross-linked polystyrene-divinylbenzene resin. Preferably, the particle is composed of microparticulate silica or alumina, since the dextran and the polystyrene-divinylbenzene resin tend to shrink or swell with solvent changes. Microparticulate silica is especially preferred, and a high-pressure liquid chromatography (HPLC) grade silica gel is a particularly suitable type of this silica. An HPLC grade silica gel having a high surface area, i.e., about 200 to 800 m²/g, and a size of about 5 to about 15 microns is an especially suitable type of silica gel. A silica gel of this type is commercially available as 10 micron Lichrosorb ® Si-60, sold by Merck, Inc. However, any chromatography grade silica gel would be suitable.

When employed in the anion exchange composition, the microparticulate silica can be used in an aqueous buffer solution of pH about 1 to about 8; alumina can be used in an aqueous buffer solution of pH about 1 to about 10; a cross-linked dextran can be used in an aqueous buffer solution of pH about 2 to about 12; and a cross-linked polystyrene-divinylbenzene resin can be used in an aqueous buffer solution of any pH. Microparticulate silica, alumina, cross-linked dextrans and cross-linked polystyrene-divinylbenzene resins are generally well known to those skilled in the art.

A suitable tetra-substituted silane which can be modified to form a weak anion exchange composition is N-2-aminoethyl-3-aminopropyl trimethoxysilane (AEAPS). This material may also be named as N-[2-(trimethoxysilyl)-ethyl]-1,3-propanediamine. Silanes may be used which are of the following general formula:

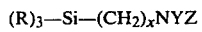

$$(R)_3-Si-(CH_2)_xNYZ$$

where R=alkyl or alkoxy, preferably of 1 to 5 carbon atoms, x is an integer of 2 or 3, and Y and Z are hydrogen, alkyl, substituted alkyl, or an alkyl amine.

In the preferred silica-containing weak anion exchange composition, the relatively hydrophobic organic center portion of the composition provides protection to the silica inner portion against gradual attack by an aqueous solvent by shielding the silica from the aqueous solvent. This shielding effect exists regardless of the type of particle selected, but is more important for certain of the particle types such as silica. Also, with this preferred silica-containing embodiment of the weak anion exchange composition, negatively charged and polar silanol groups are eliminated from the silica surface by tying these groups to a covalent bond. The elimination of the disadvantages associated with silica avoid the adsorption and clogging problems experienced with prior art coated or bare porous particle compositions.

METHOD OF MANUFACTURE

The present invention provides a process for the manufacture of a weak anion exchange composition using an inert particle as described above, and especially microparticulate silica of the type described. Preferably, this silica is a high-pressure liquid chromatography gel, and preferably this silica has a size of about 5 to about 10 microns. An especially suitable type of HPLC grade silica gel has a high surface area, i.e., about 200 to 800 m²/g, and a size of about 5 to about 10 microns. A suitable commercially available silica gel for this purpose is 10-micron Lichrosorb ® Si-60, sold by Merck. However, the silica may be any chromatrographic grade silica gel.

In the initial step of this process, the tetra-substituted silane, e.g., N-2-aminoethyl-3-aminopropyl trimethoxysilane (AEAPS) is reacted with an aqueous slurry of the silica. This reaction is conducted for a time and at a temperature sufficient to produce a product comprising AEAPS covalently bonded to the silica. A sufficient time and temperature would be 2 to 4 hours at room temperature, or from about 20° to 50° C. Suitably, the reaction is carried out at about room temperature for about 2 hours. In preparing the aqueous slurry of the silica to which AEAPS is suitably added, an amount of silica needed to form about a 5 to about a 15% by weight, preferably about a 10% by weight slurry, is advantageously prepared in water. An excess of AEAPS to reactive silanol sites on the silica is suitably used, with an about two-fold excess being preferred.

In the next step of this process, the product is recovered, washed and dried. Recovery is advantageously carried out by filtering the resulting reaction slurry of the preceding step. Suitably, the slurry is filtered through a sintered glass filter funnel having a pore size smaller than the particle size, and the product is recovered as a filter cake. The filter cake is washed using a series of solvents to remove solvent-soluble impurities. An advantageous series of solvents comprises water, methanol, tetrahydrofuran and then methanol again. About 250–500 milliliters of each of these solvents are suitably used in the washing. Then, the filter cake is dried according to conventional procedures. The dried product is then slurried with a balanced density solvent system or any other appropriate packing solvent and packed into the column at high pressure.

As a final step, the covalently bonded tetra-substituted silane is modified to a weak anion exchange resin by reaction with an acid, most preferably phosphoric acid, although acids such as acetic acid, formic acid, boric acid or sulfuric acid may be used.

METHODS OF USE

The weak anion exchange compositions of the present invention are useful for separation of polyfunctional compound mixtures and especially for separation of isomers of such compounds. This weak anion exchange composition is a useful column packing material for columns in liquid chromatographic systems such as that described in U.S. Pat. No. 3,985,021 by Achener, et al. The present invention acts not only as a weak anion exchanger, but its diamino functional group acts as a chelating agent selectively retaining multi-functional compounds by dipolar interaction. Compounds which are especially suitable for use on the present invention include nucleic acid components, dicarboxylic acids and amino acids.

It is often necessary in biological samples to analyze bases, nucleosides, and nucleotides simultaneously, which necessitates the use of ion exchange separations. It previously had been difficult to achieve conditions for isocratic ion exchange separation of nucleotides under which nucleosides are also resolved; using aqueous buffers, nucleosides are generally poorly retained. With the silicabased ion exchange of this invention, addition of an organic modifier to the mobile phase decreases the absolute solubility of solutes in the mobile phase and thus increases retention times of nucleosides and bases. An organic modifier also serves to increase the relative affinity of deoxynucleosides for the stationary phase compared to ribo compounds, enhancing the resolution of the two classes. Gradient programming may then be used to elute the more highly charged nucleotides by increasing the ionic strength and pH of the mobile phase. Complete isocratic separation of a mixture of four bases and four nucleosides can be accomplished using a mixture of 20% 0.01 M $KH_2PO_4$ (pH 2.85)—80% acetonitrile. By increasing both the molarity and pH of the aqueous mobile phase, it was possible to resolve a complex mixture of nucleoside mono-, di-, and tri-phosphates.

The separation of mixtures of nucleosides and deoxynucleosides or nucleotides and deoxynucleotides was readily obtained isocratically. The separation of a mixture of nucleosides and deoxynucleosides was achieved by elution with 82% acetonitrile–18% 0.0125 M $KH_2PO_4$, whereas the separation of a mixture of nucleotides and deoxynucleotides was accomplished by elution with 40% acetonitrile–60% 0.01 M $KH_2PO_4$ (pH 2.85). A mixture of nucleosides, nucleotides, and deoxynucleotides was partially resolved isocratically using an aqueous mobile phase.

The effect of mobile phase pH and addition of organic modifiers upon retention of a wide range of nucleic acid constituents was investigated. In some cases (e.g., 2'-and 3'-cytidine monophosphate), changing the pH provided partial resolution of coeluting compounds, while addition of acetonitrile allowed separation of the less polar bases and nucleosides. An excellent separation of nucleosides, nucleotides, deoxynucleosides, and deoxynucleotides was achieved using a gradient elution of decreasing acetonitrile concentration. This technique was also used to analyze the nucleic acid constituents in an extract of Balb-C mouse liver.

EXAMPLE I

Specific examples of the present invention are set forth below. Unless otherwise indicated, all percentages are by weight.

A weak anion exchange material according to the present invention is prepared by the following process. A slurry in distilled water of 25 grams of 10-micron Lichrosorb ® Si-60 (a microparticulate silica gel sold by Merck, Inc., which has a size of 10 microns) is prepared. To the slurry there is added 25 milliliters of N-2-aminoethyl-3-aminopropyl trimethoxysilane. The resulting slurry is stirred at room temperature for 2 hours. After the reaction is completed, the slurry is then filtered on a medium sintered glass filter funnel. There is recovered on the funnel as a filter cake a product comprising N-2-aminoethyl-3-aminopropyl silyl groups covalently chemically bonded to the silica gel. This product is N-2-aminoethyl-3-aminopropyl silica. The filter cake is washed with 500 milliliters of each of the following solvents, in turn: water, methanol, tetrahydrofuran, and then methanol again. The washed cake is then dried.

A 5% slurry of the N-2-aminoethyl-3-aminopropyl silica in a 60/40 tetrabromoethane/tetrachloroethylene solvent system is packed in a 4 mm×30 cm column at 10,000 psi. The completed column is washed with 50 ml of each of the following solvents, in turn: methanol and water; 60 ml of 0.1 M phosphoric acid; and then finally washed with 100 ml of water, to prepare the anion exchange resin.

EXAMPLE II

Separation of Ribonucleotides

The mono-, di-, and tri-phosphate nucleotides of adenine, cytosine, uracil and guanine are the intermediates in the biosynthesis and catobolism of ribosomal, transfer and messenger ribonucleic acids (r-RNA, t-RNA, m-RNA), while the relative amounts of the adenine ribonucleotides reflect the energy state of the cell. The gradient separation of these nucleotides is achieved using the anion exchange composition of Example I. High surface coverage of the column provides excellent long-term stability in the pH 2–5 phosphate buffers used in nucleotide separations. This separation is achieved using the slurry packed column described in Example I (the exchange composition), 4 mm×30 cm, at a rate of 120 ml/hr. Elution was obtained under pressure using 0.01 M $KH_2PO_4$ at a pH of 2.85 and 0.75 M $KH_2PO_4$ at a pH of 4.4.

EXAMPLE III

Separation of Ribo- and Deoxyribonucleic Acid Components

Deoxyribonucleosides and deoxyribonucleotides are the building blocks of DNA (deoxyribonucleic acid) found in the chromosomes of most living organisms. Resolution of ribo- and deoxyribonucleic acid components is important in the study of nucleotide pools and nucleoside patterns in disease states. Excellent resolution of these species is accomplished using the anion exchange composition of Example I and a column similar to Example II. The rate was 120 ml/hr and elution was accomplished under pressure with; (a) 80% acetonitrile—20% 0.01 M $KH_2PO_4$ at pH 2.85; and (b) 40% acetonitrile—60% 0.01 M $KH_2PO_4$ at a pH 2.85. The separation of ribo- and deoxyribonucleosides and monophosphate nucleotides was also accomplished on the same type of column in a gradient separation using 80% acetonitrile—20% 0.01 M $KH_2PO_4$ at a pH of 2.85, and 0.01 M $KH_2PO_4$ at a pH of 2.85.

The addition of acetonitrile to the aqueous buffer mobile phase facilitates separation of ribo-deoxyribo-analogs. Unlike separations on polystyrene resin-based ion exchangers in which nucleosides and monophosphate nucleotides elute under similar mobile phase conditions, these two classes of compounds elute in distinct regions of a chromatogram with the column.

EXAMPLE IV

Separation of a Perchloric Acid

Extract of Balb-C Mouse Liver

A perchloric acid extract comprising 2 mg. of Balb-C mouse liver was carried out using the anion exchange composition of Example I in a slurry packed column, 4 mm×30 cm, under pressure at a rate of 120 ml/hr. Elution was accomplished with solutions comprising 80% acetonitrile—20% 0.01 M $KH_2PO_4$ at a pH of 2.85 and 0.01 M $KH_2PO_4$ at a pH of 2.85.

EXAMPLE V

Separation of Nucleotide Isomers

Although di- and tri-phosphate nucleotides are important in nucleic acid synthesis and in many metabolic pathways (e.g., role of ATP), ribo- and deoxyribonucleic acids are composed exclusively of monophosphate nucleotides. Enzymatic hydrolysis of DNA or RNA yields either 3' or 5' monophosphate nucleotides, dependent on the enzymes used. Unlike DNA, RNA is hydrolyzed by weak alkali, yielding 2',3'-cyclic monophosphate nucleotides. Stronger alkali yields a mixture of 2' and 3' monophosphate nucleotides. Thus, study of the structure of nucleic acids and gene sequencing research requires the separation of monophosphate nucleotide isomers. Moreover, the important role played by cyclic nuicleotide monophosphates in modulation of enzyme function and gene expression and in mediation of hormone action requires discrimination of this species from the 2',3' or 5' isomers.

These species were separated using the anion exchange composition of Example I slurry packed in a 4 mm×30 cm column. The monophosphate nucleotide isomers were separated at a flow rate of 120 ml/hr with elution accomplished with 0.01 M $KH_2PO_4$ at a pH of 2.95. The nucleotide monophosphates were separated using a flow rate of 2.0 ml/min with the mobile phase being 0.01 M $KH_2PO_4$ at a pH of 3.

The invention has been described with reference to certain preferred embodiments. However, as obvious variations thereon will become apparent to those skilled in the art, the invention is not considered to be limited thereto.

What is claimed is:

1. A method of separating the components of a biological sample, said method comprising the steps of:
   (a) placing the biological sample in a column packed with a weak anion exchange composition comprising an inert porous particle having a size of about 5 to about 20 microns, and a modified tetra-substituted silane material of the general formula $$R_3—Si—(CH_2)_x—NYZ$$

wherein R is an alkyl or alkoxy, having 1 to 5 carbon atoms, x is an integer of 2 or 3, and Y and Z are hydrogen, alkyl, substituted alkyl, or an alkyl amine; said modified tetra-substituted silane material having been fixedly attached by covalent chemical bonding to the surface of said particle; with said modified tetra-substituted silane material fixedly attached by covalent bonding having been washed with an acid to produce said weak anion exchange composition, and;
   (b) separating said biological sample into its components using a solvent system comprising an aqueous buffer.

2. The method of claim 1 wherein said column is a high-pressure liquid chromatography column.

3. The method of claim 2 wherein the particle of which the weak anion exchange composition is comprised is selected from a group consisting of microparticulate silica, alumina, a cross-linked dextran, and a cross-linked polystyrene-divinylbenzene resin.

4. The method of claim 3 wherein the particle of which said weak anion exchange composition is comprised is microparticulate silica.

5. The method of claim 4 wherein said silica is a high-pressure liquid chromatography grade silica gel.

6. The method of claim 2 wherein said weak anion exchange material is a phosphate group, and said weak anion exchange composition is phosphato-N-2-aminoethyl-3-aminopropyl silica.

7. The method of claim 2 wherein the said biological sample separated by said weak anion exchange composition is comprised of members of a group consisting of nucleic acid components, amino acids, and dicarboxylic acids.

8. The method of claim 7 wherein the said biological sample separated by said weak anion exchange composition is a mixture of nucleic acid components.

9. A method of performing liquid chromatography comprising placing a solution of a sample comprising a mixture of polyfunctional compounds and isomers thereof on the head of a chromatographic column, flowing a solvent system through said chromatographic column, said chromatographic column being packed with a packing material comprising a weak anion exchange composition, said weak anion exchange composition comprising an inert porous particle having a size of about 5 to about 20 microns, and a modified tetra-substituted silane material of the general formula $$R_3—Si—(CH_2)_x—NYZ$$

wherein R is an alkyl or alkoxy, having 1 to 5 carbon atoms, x is an integer of 2 or 3, and Y and Z are hydrogen, alkyl, substituted alkyl, or an alkyl amine; said particle with said modified tetra-substituted silane material fixedly attached by covalent bonding having been washed with an acid to produce said weak anion exchange composition, said chromatographic column packing being capable of simultaneous separation of said mixtures.

10. A liquid chromatographic column comprising an elongated tube, a weak anion exchange composition fixedly packed into said tube, said weak anion exchange composition comprising an inert porous particle having a size of about 5 to about 20 microns, and a modified tetra-substituted silane material of the general formula $$R_3—Si—(CH_2)_x—NYZ$$

wherein R is an alkyl or alkoxy, having 1 to 5 carbon atoms, x is an integer of 2 or 3, and Y and Z are hydrogen, alkyl, substituted alkyl, or an alkyl amine; said particle with said modified tetra-substituted silane material fixedly attached by covalent bonding having been washed with an acid to produce said weak anion exchange composition; said weak anion exchange composition being capable of simultaneous separation of mixtures of polyfunctional compounds and isomers thereof in a time on the order of three hours.

11. In a liquid chromatographic system capable of separation of polyfunctional compounds and isomers thereof the improvement comprising a chromatographic column comprising a tube containing a weak anion exchange composition; said weak anion exchange composition comprising an inert porous particle having a size of about 5 to about 20 microns, and a modified tetra-substituted silane material of the general formula $$R_3—Si—(CH_2)_x—NYZ$$

wherein R is an alkyl or alkoxy, having 1 to 5 carbon atoms, x is an integer of 2 or 3, and Y and Z are hydrogen, alkyl, substituted alkyl, or an alkyl amine; said particle with said modified tetra-substituted silane material fixedly attached by covalent bonding having been washed with an acid to produce said weak anion exchange composition; said weak anion exchange composition enabling simultaneous separation of mixtures of polyfunctional compounds and isomers thereof by HPLC techniques in a time on the order of three hours.

12. A method of performing liquid chromatography comprising placing a solution of a sample comprising a mixture of polyfunctional compounds and isomers thereof on the head of a chromatographic column, flowing a solvent system through said chromatographic column, said chromatographic column being packed with a packing material comprising a weak anion exchange composition, said weak anion exchange composition comprising an inert porous particle having a size of about 5 to about 20 microns, and a modified tetra-substituted silane material of the formula

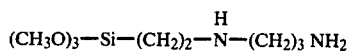

said particle with said modified tetra-substituted silane material fixedly attached by covalent bonding having been washed with an acid to produce said weak anion exchange composition, said chromatographic column packing being capable of simultaneous separation of said mixtures.

13. A liquid chromatographic column comprising an elongated tube, a weak anion exchange composition fixedly packed into said tube, said weak anion exchange composition comprising an inert porous particle having a size of about 5 to about 20 microns, and a modified tetra-substituted silane material of the formula

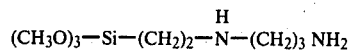

said particle with said modified tetra-substituted silane material fixedly attached by covalent bonding having been washed with an acid to produce said weak anion exchange composition, said weak anion exchange composition being capable of simultaneous separation of mixtures of polyfunctional compounds and isomers thereof in a time on the order of three hours.

14. In a liquid chromatographic system capable of separation of polyfunctional compounds and isomers thereof the improvement comprising a chromatographic column comprising a tube containing a weak anion exchange composition; said weak anion exchange composition comprising an inert porous particle having a size of about 5 to about 20 microns, and a modified tetra-substituted silane material of the formula

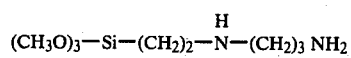

said particle with said modified tetra-substituted silane material fixedly attached by covalent bonding have been washed with an acid to produce said weak anion exchange composition; said weak anion exchange composition enabling simultaneous separation of mixtures of polyfunctional compounds and isomers thereof by HPLC techniques in a time on the order of three hours.

* * * * *